(12) United States Patent
Doerr et al.

(10) Patent No.: US 8,878,532 B2
(45) Date of Patent: Nov. 4, 2014

(54) SHIELDING APPARATUS AND SHIELDING STRUCTURES FOR MAGNETIC RESONANCE IMAGING AND METHOD FOR OPERATING A MAGNETIC RESONANCE IMAGING SCANNER

(75) Inventors: Thomas Doerr, Berlin (DE); Ingo Weiss, Berlin (DE)

(73) Assignee: Biotronik SE & Co. Kg

( * ) Notice: Subject to any disclaimer, the term of this patent is extended or adjusted under 35 U.S.C. 154(b) by 494 days.

(21) Appl. No.: 13/280,006

(22) Filed: Oct. 24, 2011

(65) Prior Publication Data

US 2012/0105059 A1 May 3, 2012

Related U.S. Application Data

(60) Provisional application No. 61/407,479, filed on Oct. 28, 2010.

(51) Int. Cl.
| G01R 33/48 | (2006.01) |
| G01R 33/44 | (2006.01) |
| A61N 1/16 | (2006.01) |
| A61N 1/04 | (2006.01) |
| A61N 1/37 | (2006.01) |
| G01R 33/422 | (2006.01) |

(52) U.S. Cl.
CPC ............... *A61N 1/16* (2013.01); *A61N 1/0484* (2013.01); *A61N 1/3718* (2013.01); *G01R 33/422* (2013.01)
USPC .......................................... 324/307; 324/318

(58) Field of Classification Search
CPC ......... A61N 1/0484; A61N 1/08; A61N 1/16; G01R 33/422; G01R 33/288
USPC ................... 324/307, 309, 318, 322
See application file for complete search history.

(56) References Cited

U.S. PATENT DOCUMENTS

| 2005/0113676 A1* | 5/2005 | Weiner et al. ................. 600/421 |
| 2006/0264137 A1* | 11/2006 | Ishihara et al. ............... 442/304 |
| 2008/0023010 A1 | 1/2008 | Inman et al. |
| 2008/0060843 A1* | 3/2008 | Ginanneschi ................. 174/378 |
| 2011/0140695 A1* | 6/2011 | Hollis et al. .................. 324/307 |

FOREIGN PATENT DOCUMENTS

| DE | 20113511 U1 | 4/2002 |
| EP | 1205589 A1 | 5/2002 |
| JP | 9310208 A | 2/1997 |
| WO | 01/37286 A1 | 5/2001 |

OTHER PUBLICATIONS

European Search Report received fro EP Application Serial No. 11184601.0, dated Feb. 13, 2012, 7 pages.

* cited by examiner

*Primary Examiner* — Melissa Koval
*Assistant Examiner* — Rishi Patel
(74) *Attorney, Agent, or Firm* — ARC IP Law, PC; Joseph J. Mayo

(57) ABSTRACT

One or more embodiments of the invention relate to a shielding apparatus for shielding at least one at least partially metallic implant in the body of a patient during an examination by magnetic resonance imaging, which can be attached temporarily on or in the vicinity of the body of the patient and comprises a shielding material, which is suited to attenuate radio frequency alternating electromagnetic fields.

20 Claims, 8 Drawing Sheets

SHIELDING APPARATUS AND SHIELDING STRUCTURES FOR MAGNETIC RESONANCE IMAGING AND METHOD FOR OPERATING A MAGNETIC RESONANCE IMAGING SCANNER

This application claims the benefit of U.S. Provisional Patent Application 61/407,479 filed on 28 Oct. 2010, the specification of which is hereby incorporated herein by reference.

BACKGROUND OF THE INVENTION

1. Field of the Invention

Embodiments of the invention refer to the field of medical technology and relates to a shielding apparatus and shielding structures for magnetic resonance imaging and to a method for operating a magnetic resonance imaging scanner.

2. Description of the Related Art

In nuclear magnetic resonance or magnetic resonance imaging (MRI=Magnetic Resonance Imaging), powerful static magnetic fields force atom nuclei to perform a precision movement about the field direction and the nuclei are excited by resonance by radio frequency alternating electromagnetic fields. After the alternating fields are switched off, the nuclei return in the starting directions thereof, wherein the decay times (relaxation times) are characteristic of different tissue types, thereby enabling precise imaging.

Today, MRI examinations are part of the daily routine in radiological diagnostics, posing no risk for the patients under normal examination conditions, apart from an occasional decreased sense of well-being. However, an increasing number of patients has implants which are made entirely or partially of a metallic material and can cause problems during the examination, and in the worst case can even injure the patients. The material that is used and the geometry of the implant, as well as the position thereof in relation to the radio frequency alternating fields that are employed, play a role. Some implants, for example, function very well as antennas for the alternating fields and heat up considerably due to the induction currents that are generated. Consequently, thermal damage to the surrounding tissue may ensue. On the other hand, the radio frequency alternating fields may trigger a malfunction in electronic implants or an undesirable restart with preset starting parameters ("power-on reset").

For this reason, the diagnostic benefit of an examination by magnetic resonance imaging must be carefully weighed against the risk of disadvantageous side effects. An additional hindering aspect is that, for example, the heating of implanted electrodes depends on the respective scan parameters of the examination, and in particular on the positioning thereof in the alternating electromagnetic field, so that in clinical practice it is frequently impossible to make reliable predictions as to the effects to be expected. All these factors consequently lead to patients that have implants to be generally excluded from an examination by magnetic resonance imaging, which is a gentle process per se.

In recent times, increased efforts to solve this problem have been made. For example, new cardiac pacemaker systems have been developed, which are equipped with pacemaker electrode having a specific geometric configuration so as to counteract heating by the alternating electromagnetic fields. The disadvantage here is that these solutions are associated with additional complexity for the implants and may also impair the implant properties. In addition, patients who already have an implant still cannot be examined by magnetic resonance imaging.

BRIEF SUMMARY OF THE INVENTION

In contrast, it is a feature of the present disclosure to enable patients having an implant to undergo a magnetic resonance imaging examination without risk, without requiring special precautions on the implant for this purpose. This and other features are achieved according the proposed disclosure by a shielding apparatus and shielding structures and by a method for operating a magnetic resonance imaging scanner having the characteristics of the independent claims. Advantageous embodiments of the invention are provided by the characteristics of the dependent claims.

According to one or more embodiments of the invention, a shielding apparatus for medical use is provided, which is used to shield at least one at least partially metallic implant in the body of a patient during a magnetic resonance imaging examination (MRI examination). As it is used here, the term "implant" denotes an apparatus which is intended to remain permanently or only temporarily in the body of a patient, which can involve, for example, an electronic device such as a cardiac pacemaker or cardioverter, an electrode such as a stimulation electrode, in particular for neural stimulation, a cardiac pacemaker electrode, an ICD electrode, an electrophysiology catheter, or an electrode for measuring brain potentials or drug pumps or stents or bone implants or nails or clamps or bone clamps or the like. This list is of course not exhaustive.

The shielding apparatus according to one or more embodiments of the invention is designed such that it can be attached temporarily on or close to the body of the patient and comprises a shielding material, which is suited to attenuate radio frequency alternating electromagnetic fields during the MRI examination. In general, these are alternating electromagnetic fields having a frequency in a range above 1 MHz. For example, at a static magnetic field of 1 tesla, protons can be excited with an alternating electromagnetic field having a frequency of approximately 42 MHz, at a static magnetic field of 1.5 tesla, they can be excited with an alternating electromagnetic field having a frequency of approximately 63 MHz. The shielding material is designed so that an appreciable attenuation effect is achieved for the radio frequency alternating fields employed during the MRI examination, the effect being at least strong enough that an impairment of the implant accompanied by a potential risk for the patient is prevented. In this way, a malfunction of an electronic implant is prevented and the heating of an electrode is to be drastically reduced or minimized. Without being limited thereto, the shielding material may also achieve an attenuating effect, for example, by which the intensity relative to the intensity of the alternating field striking the shielding apparatus is reduced such that it is smaller than 50%, particularly smaller than 40%, particularly smaller than 30%, particularly smaller than 20%, particularly smaller than 10%, particularly smaller than 5%, and particularly smaller than 1%.

In order to be able to have an attenuating effect on the radio frequency alternating fields, which is to say to reduce the intensity of the alternating fields, the shielding material is electrically conductive. In general, the shielding material may be present in the form of an electrically conductive solid body, wherein it may be configured as granules and/or polymer material and/or in the form of carbon fibers. The shielding material can be present in particular as a mesh made of fibers of an electrically conductive material or as an electrically conductive foil, for example.

In order to be able to attach the shielding apparatus temporarily on or close to the body of the patient, it is advantageously designed in the form of a vest, trousers, trouser leg, ruff, cap, head mask having openings for eyes and breathing holes, or as a part that can be wound around the body or a body part of the patient. As a vest, the shielding apparatus is used in particular for shielding an implant in the thoracic region, for example a cardiac pacemaker. As trousers or a trouser leg, it is used in particular for shielding an elongated metallic vascular prosthesis or stent, which frequently have a length of at least 200 mm. As a cap or head mask, it is used in particular for shielding a so-called deep brain stimulator.

For fastening to the patient, the shielding apparatus may be provided with closures such as Velcro fasteners, for example, which are preferably made of an electrically conductive material so as to ensure complete shielding. It is also conceivable to provide the shielding apparatus with one or more adhesive points, so that it can be glued to a body surface of the patient for fixation. The shielding apparatus can be composed at least partially of breathable materials to increase the comfort for the patient. In general, the shielding apparatus can be provided for single and/or multiple uses.

In this way, the shielding apparatus according to one or more embodiments of the invention advantageously enables a simple, cost-effective MRI examination that is free of risks for the patient, without requiring special precautions on the implant. In particular patients who already have an implant can also undergo an MRI examination by way of the shielding apparatus according to one or more embodiments the invention. For example, it is also possible to perform MRI examinations on patients having a defective and/or deactivated electrode or probe. On the other hand, the shielding apparatus according to one or more embodiments the invention can also be used to protect medical staff having an implant that is made at least partially of metal.

The shielding apparatus according to one or more embodiments the invention has an attenuating effect on the radio frequency alternating electromagnetic fields used in magnetic resonance imaging. In an advantageous embodiment of the shielding apparatus according to one or more embodiments the invention, additionally the relative magnetic permeability thereof is no more than 100, particularly no more than 4, and particularly no more than 1. It may be advantageous if the shielding apparatus is made exclusively of paramagnetic and/or diamagnetic or magnetically neutral materials. As a result of this measure, it can be achieved that the shielding apparatus is transparent to the strong static magnetic fields used in the MRI examination and the magnetic gradient fields that are applied, in order to avoid a distortion of these fields and reduce or prevent artifacts. In addition, imaging can advantageously take place close to the shielding apparatus.

The shielding apparatus according to the invention is suited to at least partially, and more particular (practically) completely shield the implant of the patient against the alternating electromagnetic fields used during the MRI examination. This is achieved by the attenuating effect of the shielding material, wherein the attenuating effect of the shielding material is preferably particularly high against the alternating electromagnetic fields used during the MRI examination. In particular, it is possible for the shielding material to exhibit a frequency-independent attenuating effect, which is adapted to the radio frequency alternating electromagnetic fields of the MRI examination or to a certain scanner type (magnetic resonance imaging scanner).

In a further advantageous embodiment of the shielding apparatus according to one or more embodiments the invention, a physical and/or chemical property of the shielding material can be varied so as to vary the attenuation ability thereof for attenuating the alternating electromagnetic fields used during the MRI examination. For this purpose, it may be advantageous for the shielding apparatus to be designed such that the quantity of the shielding material or the volume of a liquid shielding material can be varied. In particular it may be advantageous if the shielding material can be partially or completely removed from the shielding apparatus, so that the shielding material can be at least partially replaced. In this way, the attenuating effect can be specifically adjusted in accordance with the patient and/or the specific scanning parameters and/or the scanner type that is used. In addition, a thickness (this being a dimension perpendicular to the body surface of the patient) of the shielding apparatus can be adjusted as needed by a quantity or volume change of the shielding material. It may further be advantageous for the shielding apparatus to be configured such that the electric conductivity of the shielding material can be varied for the purpose of varying the attenuating effect. In the case of a liquid shielding material, the electric conductivity can be varied, for example, by the variable content of an ionically dissolved substance. In general, the attenuating effect of the shielding apparatus can be specifically adjusted to the needs of the user by varying the quantity and/or varying the composition and/or replacing the shielding material.

In a further advantageous embodiment of the shielding apparatus according to one or more embodiments the invention, it is suitably designed to adapt to a contour of a body surface of the patient. As a result of this measure, particularly good shielding of the implant against the alternating fields used during the MRI examination can be achieved. In addition, the comfort for the patient is increased in this way. For this purpose, the shielding apparatus may be produced from flexible or ductile material, for example. The shielding apparatus is preferably configured such that a (shortest) distance between the shielding apparatus and the body surface of the patient is no larger than 5 cm, more preferred no larger than 3 cm, and even more preferred no larger than 1 cm, at any location. With this measure, a particularly good shielding effect can be achieved against the radio frequency alternating fields. When using the shielding apparatus in the thoracic region, it is preferred when the flexibility of the shielding apparatus is such that the breathing ability of the patient is not notably impaired. In addition, the shielding apparatus may be made at least partially of breathable materials. In addition, the shielding apparatus may be filled with a gaseous and/or liquid fluid to adapt to the contour of the body surface of the patient. The liquid fluid may in particular be the shielding material.

In a further advantageous embodiment of the shielding apparatus according to one or more embodiments the invention, it is composed of a plurality of segments which are galvanically or capacitively coupled to each other. With this measure, good adaptability of the shielding apparatus to a contour of a body surface of the patient can be achieved. In addition, the segments can be specifically arranged to act as resonators for the radio frequency alternating fields used during the MRI examination and thereby improve the shielding effect for the implant.

In a particularly advantageous embodiment, suitable dimensioning of the segment results not only in good adaptability of the shielding apparatus to a contour of a body surface of the patient and the resonator properties for the radio frequency alternating fields used in the MRI examination, but also that gradient fields are at the same time allowed to pass through the shielding apparatus.

It is also particularly preferred that the capacitance between the segments ranges between 100 pF per cm$^2$ and 10 nF per cm$^2$ when the segments are capacitively coupled.

The shielding apparatus according to one or more embodiments the invention can heat up due to induction currents generated by the radio frequency alternating fields. The shielding apparatus preferably comprises a cooling device for active or passive cooling. This measure advantageously allows the comfort for the patient to be increased when using the shielding apparatus. In addition, the duration of the MRI examination, and optionally the intensity of the radio frequency alternating fields used during the examination, can be increased. The cooling device can in particular be designed as an apparatus for active ventilation. It is also conceivable to use Peltier elements that are based on the Peltier effect for active cooling, which generate or dissipate heat depending on the polarity of the applied voltage. Passive cooling can be achieved by precooled cooling elements, for example.

In a further advantageous embodiment of the shielding apparatus according to one or more embodiments the invention, the shielding apparatus is equipped with a communication device for communicating with the (electronic) implant. In this way, information can be transmitted to the implant, wherein in particular the information that the shielding apparatus according to the invention is used and an MRI examination is being conducted can be transmitted. The implant can be programmed, for example, such that it thereupon switches to an MRI operating mode, which is specifically adjusted to the MRI examination so as to prevent malfunctions.

The communication device of the shielding apparatus is preferably designed such that it can be fed power from the radio frequency alternating field of the magnetic resonance imaging scanner, so that no separate power supply for the communication device is required and it only operates while the MRI examination is actually being conducted. The activity of the communication device is thus controlled by the energy of the radio frequency alternating fields, wherein the implant is provided with the information that the imaging process or the generation of radio frequency alternating fields has ended when there is no activity of the communication device and can thus switch back to the normal operating mode.

In a further advantageous embodiment of the shielding apparatus according to one or more embodiments the invention, it comprises a marking device for marking it in a magnetic resonance image created during the examination. This measure advantageously allows an automatic image correction or artifact delineation to be carried out so as to improve the imaging quality. The marking device can in particular be configured as an RFID (RFID=Radio-Frequency IDentification) transponder, which enables automatic identification and marking by way of electromagnetic waves.

In a further advantageous embodiment of the shielding apparatus according to one or more embodiments the invention, it is designed such that the thickness thereof (this being the dimension perpendicular to a body surface of the patient) changes only slightly, if at all, when using it on the patient, as a result of the application of a mechanical force, such as by the weight of the patient. The thickness of the shielding apparatus preferably changes less than 20%. With this measure, a reliable and safe attenuating effect of the shielding apparatus can be ensured. This applies in particular to shielding apparatuses which can be filled with liquid shielding material. For this purpose, the shielding apparatus may be provided with a honeycomb structure.

In a further advantageous embodiment of the shielding apparatus according to one or more embodiments the invention, an edge region (border) of the shielding apparatus is designed such that excess heating of the body tissue of the patient is prevented by a locally increased specific absorption rate (SAR). This can be achieved, for example, by designing the shielding apparatus so that the shielding efficiency thereof, or the attenuating effect thereof, against the radio frequency alternating fields gradually decreases toward the edge, for example, and/or that a (shortest) distance between the shielding apparatus and the body surface of the patient increases toward the edge. This measure in particular allows the comfort for the patient to be increased. In addition, the duration of the examination, and optionally the intensity of the radio frequency alternating fields, can be increased.

In a further advantageous embodiment of the shielding apparatus according to one or more embodiments the invention, an edge region (border) of the shielding apparatus is designed such that the wave impedance of the radio frequency alternating fields changes only slightly from the non-shielded body tissue to the region shielded by the shielding apparatus. The wave impedance preferably changes by less than 20%, particularly preferred by less than 10%, and even more preferred by less than 5%. It is particularly preferred when a transformation or adaptation of the impedance to the shielded region occurs within the first 2 to 5 cm, starting from the edge region (border) of the shielding apparatus. With this measure, the imaging quality can be advantageously improved.

In a further advantageous embodiment of the shielding apparatus according to one or more embodiments the invention, it is provided for use in the thoracic region with electrode surfaces, which establish electric contact with the body surface when the shielding apparatus has been positioned. The electrode surfaces can be used in particular for defibrillation. The electrode surfaces are preferably connected to input leads such that they can be controlled by an external defibrillator without previously taking off the shielding apparatus. This means, for example, that on a vest-shaped shielding apparatus the leads or contact surfaces for connecting the defibrillator are advantageously disposed on the outside of the vest.

In a further advantageous embodiment of the shielding apparatus according to one or more embodiments the invention, it is designed such that it can be or is galvanically or capacitively coupled to the body surface of the patient when it is attached on or close to the patient. Such coupling can be achieved, for example, by an electrically conductive gel. In the case of a capacitive coupling, it may be advantageous when the capacitance is greater than 1 pF/m$^2$ coupling surface.

One or more embodiments of the invention further relates to a first shielding structure comprising a shielding apparatus for shielding at least one at least partially metallic implant in the body of a patient during a magnetic resonance imaging examination by way of a magnetic resonance imaging scanner. In the shielding structure, the shielding apparatus can be temporarily attached on or in the vicinity of the body of the patient and comprises a shielding material, which is suited to attenuate radio frequency alternating electromagnetic fields used during the magnetic resonance imaging examination, wherein the patient is located in a cylindrical tunnel ("patient cylinder") of the magnetic resonance imaging scanner and the shielding apparatus is designed such that it extends in the space around the shielded region of the patient in the radial direction up to the patient cylinder.

One or more embodiments the invention further relates to a second shielding structure comprising a shielding apparatus having a cylindrical outer contour for shielding at least one at least partially metallic implant in the body of a patient during a magnetic resonance imaging examination by way of a magnetic resonance imaging scanner. In the shielding structure, the shielding apparatus can be temporarily attached on or in the vicinity of the body of the patient and comprises a shielding material, which is suited to attenuate radio frequency alternating electromagnetic fields used during the magnetic resonance imaging examination, wherein the shield apparatus is disposed coaxially to a field coil for generating the alternating electromagnetic fields. The characteristics of the second shielding structure can in particular be combined with the characteristics of the first shielding structure so as to advantageously achieve further improvement in the shielding against the alternating electromagnetic fields.

One or more embodiments the invention further relates to a method for operating a magnetic resonance imaging scanner, which uses radio frequency alternating electromagnetic fields, wherein a shielding apparatus is attached on or in the vicinity of the body of the patient, said apparatus comprising a shielding material which is suited to attenuate the alternating electromagnetic fields so as to shield at least one at least partially metallic implant against the alternating electromagnetic fields.

In an advantageous embodiment of the method according to one or more embodiments the invention, the shielding apparatus is cooled at least some of the time before and/or during the MRI examination.

In a further advantageous embodiment of the method according to one or more embodiments the invention, the alternating electromagnetic fields are attenuated during an excitation phase, during which the radio frequency alternating electromagnetic fields for the resonant excitement of atom nuclei are generated, and are attenuated less or not attenuated during a readout phase, during which the excited atom nuclei relax and the emitted alternating electromagnetic fields are captured for imaging by the magnetic resonance imaging scanner. In this way, the exciting energy is attenuated so as not to influence the implant, but subsequently activated, so as not to reduce the signal returned by the atom nuclei and unnecessarily impair the image quality, in particular in the shielded region of the body.

In a further advantageous embodiment of the method according to one or more embodiments the invention, the alternating electromagnetic fields are attenuated such that magnetic resonance imaging continues to be possible in the region of the implant.

In a further advantageous embodiment of the method according to one or more embodiments the invention, scanning parameters such as intensity, frequency, and the scanning region of the alternating electromagnetic fields are adjusted during the MRI examination if the alternating electromagnetic fields are attenuated by the shielding apparatus, so as to enable optimized imaging.

One or more embodiments of the invention further relate to the use of a shielding apparatus according to one or more embodiments the invention for shielding at least one at least partially metallic implant in the body of a patient during an examination by magnetic resonance imaging.

The different embodiments and developments of the subject matters according to one or more embodiments the invention can of course be implemented alone or in arbitrary combinations.

The above characteristics and those described below can in particular be used not only in the described combinations, but also in other combinations or alone, without departing from the scope of one or more embodiments of the invention.

BRIEF DESCRIPTION OF THE DRAWINGS

One or more embodiments the invention will be explained in more detail based on exemplary embodiments, referencing the attached figures. Equivalent elements or elements with equivalent effects are denoted by the same reference numerals. In the drawings.

DETAILED DESCRIPTION OF THE INVENTION

Figure 1:
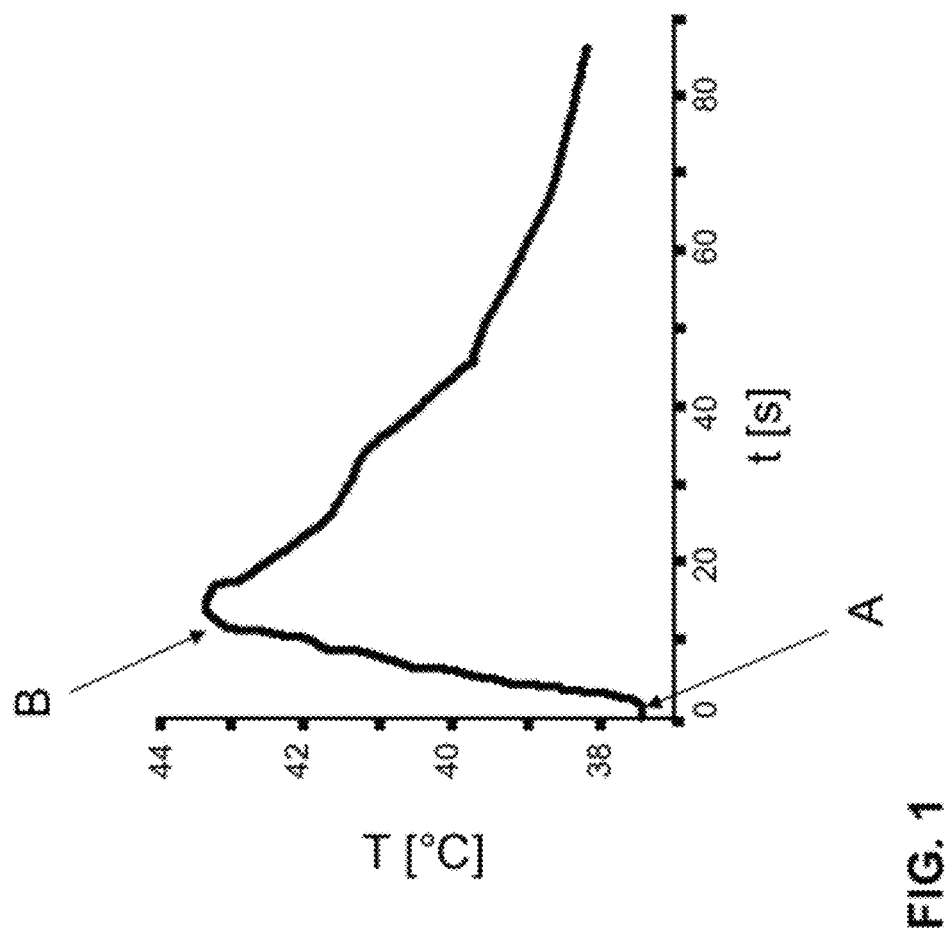
FIG. 1 is a typical temperature curve of the electrode tip of an implanted electrode during an MRI examination.

FIG. 1 shows a diagram of a typical temperature curve of the electrode tip in an implanted conventional pacemaker/ICD electrode during an MRI examination. The abscissa indicates the time (t) in seconds and ordinate the temperature T in ° C. The cause for the rise in the temperature is the electromagnetic interference (generation of induction currents). The temperature of the electrode tip thus rises rapidly when the radio frequency alternating field is switched on at the time A, with the slope of the temperature rise and the maximum temperature that can be achieved being highly dependent on the spatial position of the electrode with respect to the alternating field. In the example shown, the temperature rises to above 43° C. After the alternating field is switched off at the time B, the electrode tip cools off relatively quickly due to the relatively low thermal capacity. Because of the high temperature that the electrode tip reaches, thermal damage to the surrounding tissue cannot be excluded.

Figure 2A:
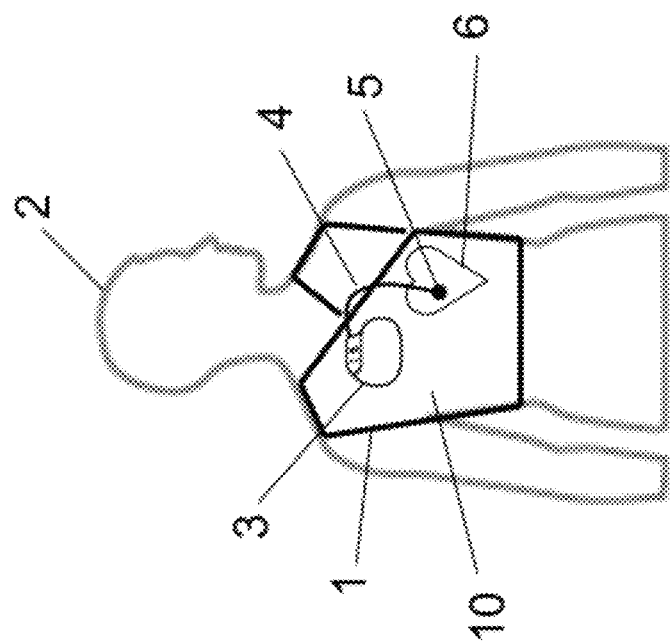
FIGS. 2A-2B are schematic illustrations of a patient having an implant, without a shielding apparatus (FIG. 2A) and with an exemplary shielding apparatus (FIG. 2B)
Figure 2B:
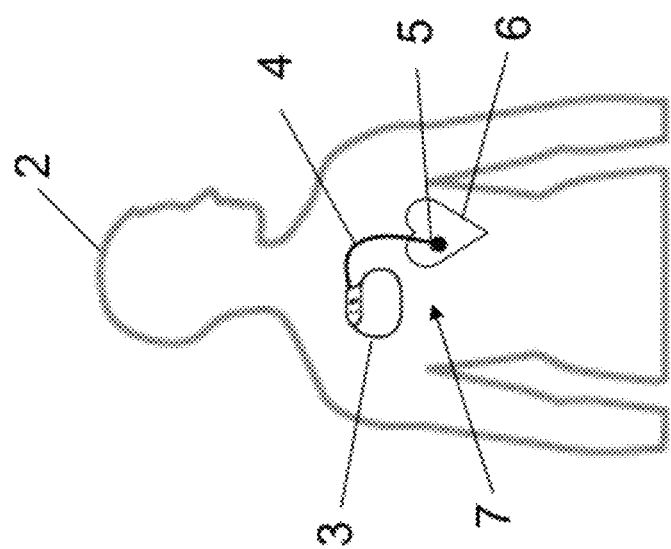

FIGS. 2A and 2B show based on schematic illustrations a patient 2 having an electronic implant, which here is designed as a pacemaker 3, for example. FIG. 2A shows the patient 2 without the shielding apparatus 1 according to one or more embodiments of the invention, and FIG. 2B shows the patient 2 with the shielding apparatus 1 applied. The pacemaker 3 is connected to the heart 6 of the patient by an electrode lead 4. For this purpose, the electrode lead 4 comprises a distal section, which passes the right atrium, for example, and is positioned with a distal end or electrode tip 5 inside the right ventricle. Electrode surfaces, which are not shown in detail, in the region of the electrode tip 5 can be used for sampling and/or stimulation purposes (antibradycardic stimulation). The pacemaker 3 can thus capture electric signals of the heart 6 and emit electric pulses, so as to trigger contractions of the heart 6 as needed. Instead of a pacemaker 3, an ICD (cardioverter/defibrillator) could also be implanted, for example. This is an electronic device which can generate shock pulses, for example in order to end life-threatening atrial fibrillation.

Without corresponding counter-measures, an MRI examination above all poses the risk of heating of the electrode tip 5 having a small surface by the radio frequency alternating fields used in the process. This heating may result in a rise in the stimulation thresholds, an impairment of the function (malsensing or oversensing) and/or lasting damage to the surrounding heart muscle tissue. The consequence may be an electrode dislocation and/or heart muscle perforation. In addition, it is possible that the pacemaker 3 paces incorrectly or treatment is inhibited.

These undesirable consequences can be avoided by the shielding apparatus 1 shown in FIG. 2B. The shielding apparatus 1 here is shown in the form of a vest, for example, which can be easily and safely applied as a winding part in the region of the thorax 7 of the patient 2 for the duration of the MRI examination. The shielding apparatus 1 completely covers the region of the implanted pacemaker 3 and the related electrode lead 4 around the patient 2. The shielding apparatus 1 can be fastened to the patient 2 by a Velcro fastener, for example, which is not shown in detail. The Velcro fastener is preferably made at least partially of an electrically conductive material, so as to ensure complete shielding also in this region. As an alternative, it would likewise be possible for the shielding apparatus to be configured, for example, in the manner of a bandage or as a glue-on single-use item.

The shielding apparatus 1 is designed such that it absorbs a significant portion of the radio frequency alternating electromagnetic fields used during the MRI examination and thereby shields the pacemaker 3 and the electrode lead 4 against the alternating fields. For this purpose, the shielding apparatus 1 comprises an electrically conductive shielding material 10, for example an electrically conductive polymer or a meshwork composed of metal or carbon fiber threads, which covers the shielding apparatus 1 at least partially, and preferably completely. It is also conceivable that the shielding apparatus 1 comprises at least one hollow space, which is filled with an electrically conductive, liquid shielding material 10. This variant has the particular advantage that the electric conductivity and/or the volume of the fluid or shielding material 10 and/or the type thereof can be selected freely and adjusted specifically to the needs of the users, which is to say to the desired attenuating effect for specific scanning parameters. The electrically conductive fluid can in particular also be replaced with another fluid, which has better or poorer conductivity or is not electrically conductive. In addition, the shielding apparatus 1 can be easily adapted to the contour of the body surface of the patient 2 in order to achieve an optimal shielding effect. The relative magnetic permeability of the shielding apparatus 1 is no more than 100, in particular no more than 4, in particular no more than 1, so that the apparatus is transparent to the strong static magnetic field used during the MRI examination as well as to the magnetic gradient fields that are applied.

In a particularly advantageous manner, the alternating electromagnetic fields can be attenuated during the MRI examination during an excitation phase, during which the radio frequency alternating electromagnetic fields for the resonant excitement of atom nuclei are generated, and can be attenuated less or not attenuated at all during a readout phase, during which the excited atom nuclei relax and the emitted alternating electromagnetic fields are captured for imaging by the magnetic resonance imaging scanner. In this way, a change of the electric conductivity and/or of the volume of the liquid shielding material 10 is easy to achieve.

It is also advantageous when the shielding apparatus 1 is equipped with a cooling device (not shown) for actively or passively cooling the same, so as to increase the comfort for the patient and avoid excessive heating of the shielding apparatus 1 during longer MRI examinations. Passive cooling can be achieved by cooling elements, for example.

Figure 3:
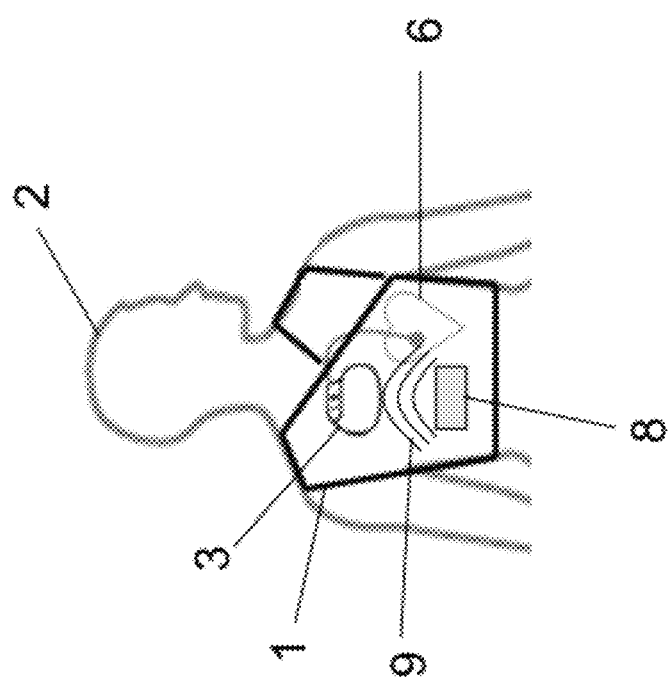
FIG. 3 is a schematic illustration of a patient having an implant to illustrate a further exemplary shielding apparatus.

FIG. 3 shows a variant in which the shielding apparatus 1 configured as a vest is equipped with a communication device 8. The communication device 8 is able to transmit an electric signal 9 wirelessly to the pacemaker 3, wherein in this way the information that the shielding apparatus 1 is used and an MRI examination is being conducted can be transmitted. The pacemaker 3 can be programmed, for example, such that it thereupon switches to an MRI operating mode, which is specifically adjusted to the MRI examination so as to prevent malfunctions. For this purpose, the communication device 8 is equipped with means, which are not shown in detail, for detecting a static magnetic field and/or a gradient field and/or a radio frequency electromagnetic field, and with means for generating and transmitting the signals 9, which preferably contain a code that the pacemaker 3 can recognize, so as to temporarily preferably switch the same into the MRI operating mode. The communication device 8 can, for example, obtain the necessary power from the fields used during the MRI examination, wherein it is equipped for this purpose with means for generating power and for the temporary storage of power (such as a capacitor, storage battery), these means not being shown. The activity of the communication device 8 is thus controlled exclusively by external energy, wherein the pacemaker 3 is provided with the information that the imaging process or the generation of radio frequency alternating fields has ended when there is no activity of the communication device 8 and can thus switch back to the normal operating mode. As an alternative, it would also be possible for the communication device 8 to be supplied by a power storage device (for example a battery) of its own.

Figure 4A:
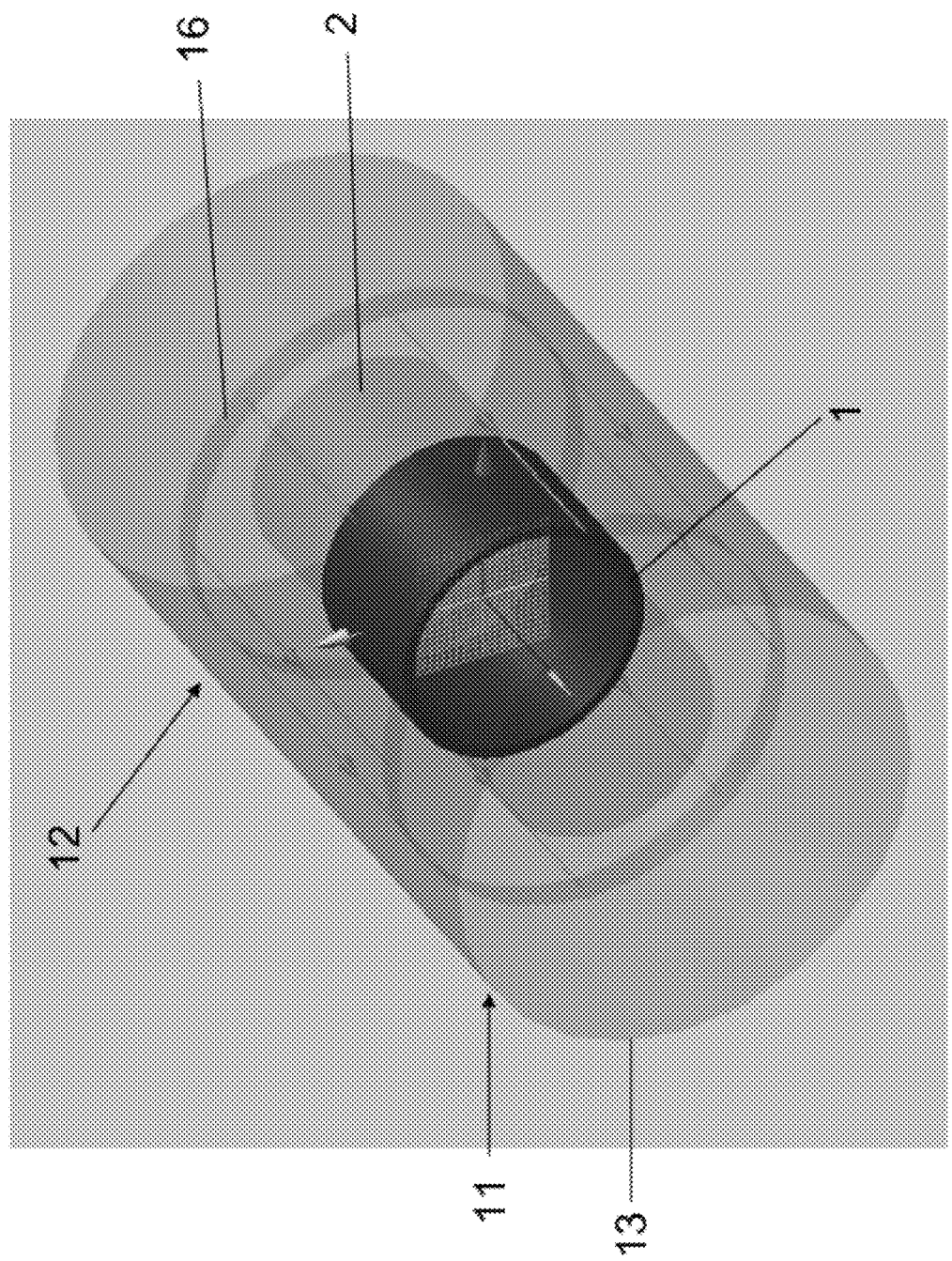
FIGS. 4A-4B are schematic illustrations to illustrate an exemplary shielding structure.
Figure 4B:
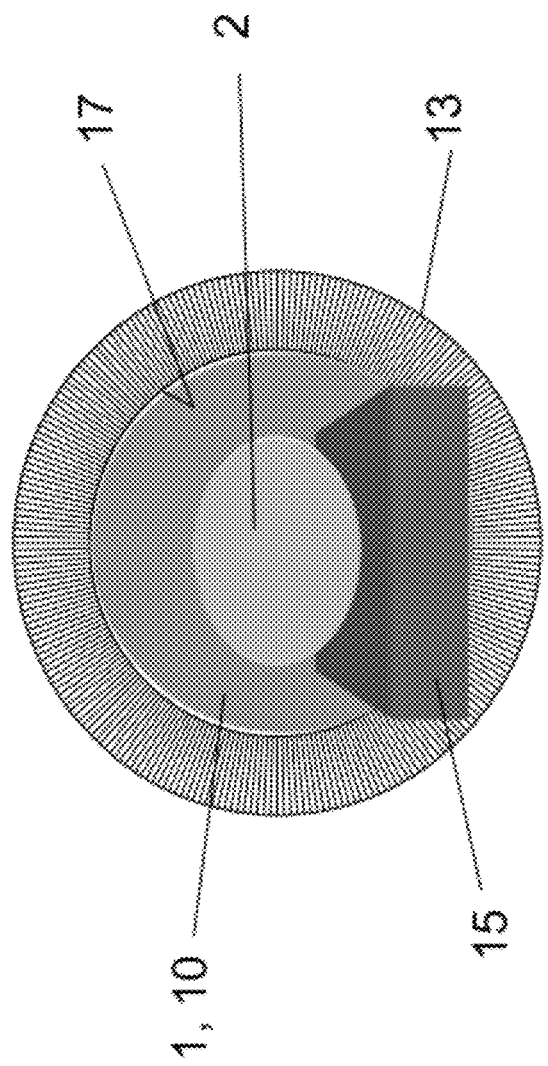

FIGS. 4A and 4B show another exemplary embodiment of the invention in a schematic illustration. FIG. 4A is a (transparent) perspective projection and FIG. 4B is a vertical section through FIG. 4A. According to these figures, a shielding structure denoted overall with reference numeral 11 comprises a magnetic resonance imaging scanner 12 having a tubular receptacle or patient cylinder 13, in which a schematically illustrated patient 2 can be placed on an examination table 15 for the examination. An alternating electromagnetic field can be generated for the MRI examination by way of a cylindrical radio frequency resonator 16. The patient cylinder 13 is used to shield against the alternating fields toward the outside. A shielding apparatus 1 is disposed on the body of the patient 2, which as in the exemplary embodiments described above can be configured, for example, as a vest for shielding an implant in the thoracic region. It is essential that the shielding apparatus 1 is filled, for example, with a liquid shielding material 10 so far that it rests against the body surface of the patient 2 and additionally completely fills in the space 14 up to the inside wall 17 of the patient cylinder 13. In this way, a particularly effective shielding effect can be achieved. With the spatially movable examination table 15, the patient 2 can optionally be moved into a desired position inside the patient cylinder 13, for example centered inside the shielding apparatus 1. The shielding apparatus 1 has a cylindrical outer contour, which here can be disposed, for example, coaxially to the radio frequency resonator 16, whereby a particularly good shielding effect can be achieved.

Figure 5B:
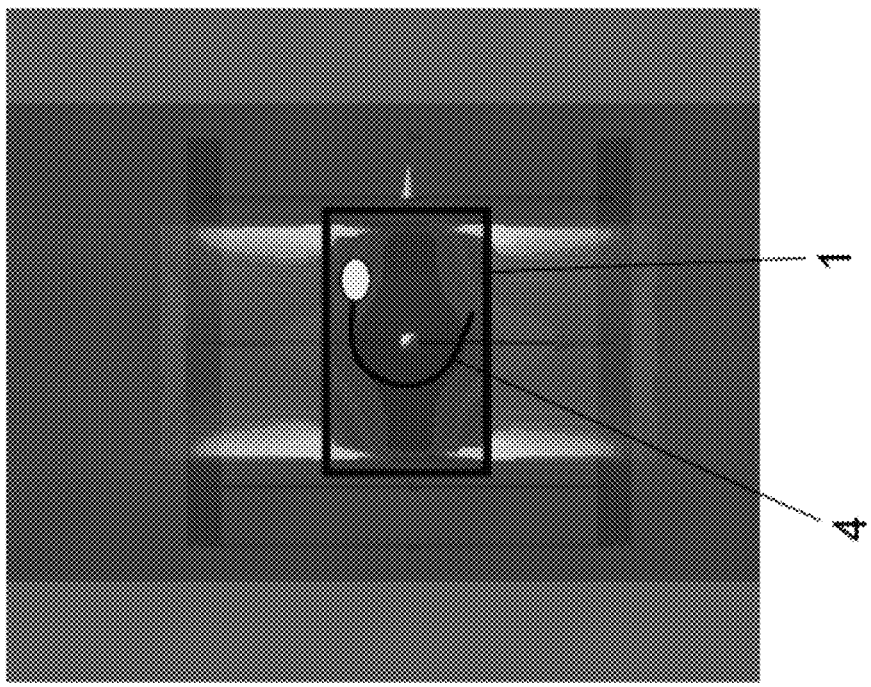
FIGS. 5A-5B are computer simulations to illustrate the effect of the shielding apparatus.
Figure 5A:
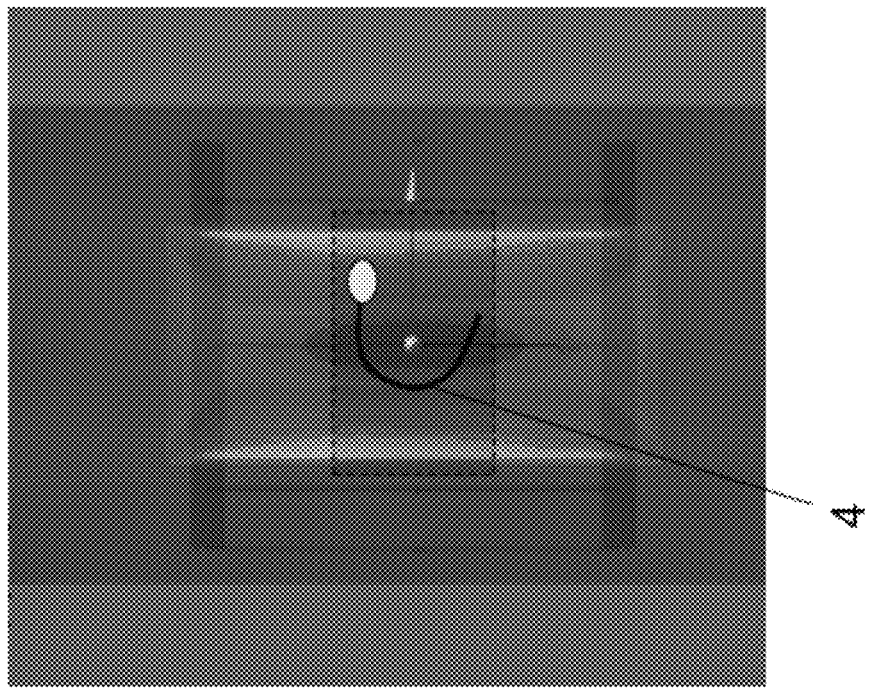

For a situation as that illustrated in FIGS. 4A and 4B, FIGS. 5A and 5B show a distribution of the energy densities (SAR=specific absorption rate) in W/kg generated in the body of the patient 2 in the region of the electrode lead 4 during the MRI examination, wherein FIG. 5A shows the situation without the shielding apparatus 1 and FIG. 5B shows the situation with the shielding apparatus 1. These are based on a computer simulation in which the patient 2 is located centrally in the scanner or patient cylinder 13 (worst case scenario). The figures clearly show the energy densities that are present in the direct vicinity of the electrode lead 4 and the advantageous effect that can be achieved by the shielding apparatus 1.

Figure 6B:
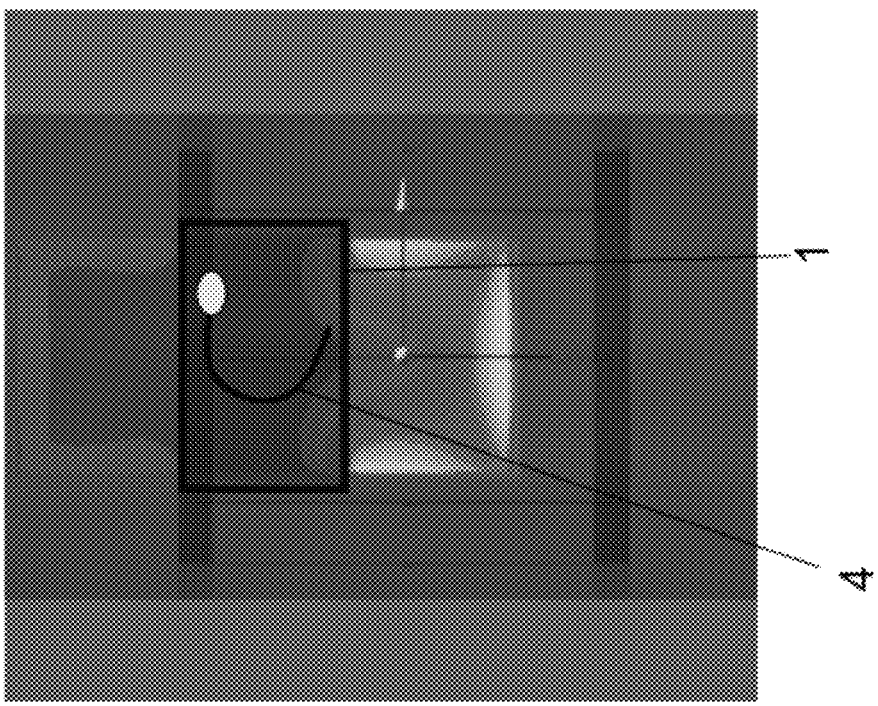
FIGS. 6A-6B are further computer simulations to illustrate the effect of the shielding apparatus.
Figure 6A:
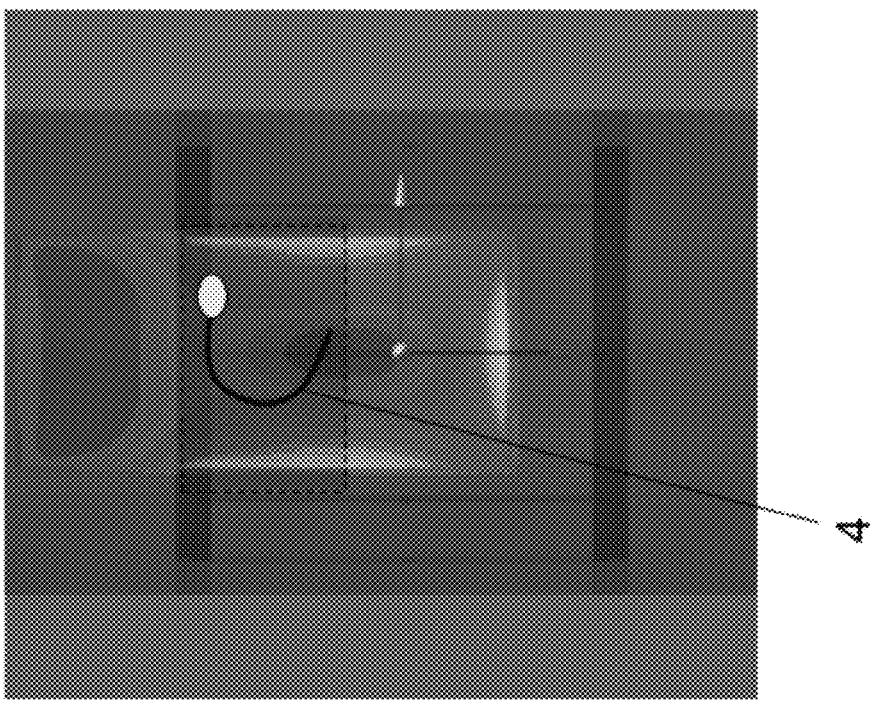

For a situation as that illustrated in FIGS. 4A and 4B, FIGS. 6A and 6B show a distribution of the energy densities (SAR=specific absorption rate) in W/kg generated in the body of the patient 2 in the region of the electrode lead 4 during the MRI examination, wherein FIG. 6A shows the situation without the shielding apparatus 1 and FIG. 6B shows the situation with the shielding apparatus 1. These are based on a computer simulation in which the patient 2 is located decentralized in the scanner or patient cylinder 13 (abdomen scan). These figures also clearly show the energy densities that are present in the direct vicinity of the electrode lead 4 and the advantageous effect that can be achieved by the shielding apparatus 1.

For the situation shown in FIGS. 4A and 4B, the following table provides the simulation results with respect to the shielding effect of the shielding apparatus 1. The following applies:

espr: relative permittivity of the filler medium or shielding material 10
sigma: conductivity in S/m
top: body region above the region being shielded
bottom: body region below the region being shielded
center: shielded region

|  | Mean SAR (mW/Kg/ 1 W scanner power) | | |
| --- | --- | --- | --- |
|  | top | center | bottom |
| without shielding apparatus | 0.89 | 1.06 | 0.81 |
| Filling_metallic | 1.08 | 0.2 | 0.98 |
| Filling_epsr3_sigma100 | 1.06 | 0.19 | 0.95 |
| Filling_epsr3_sigma1000 | 1.08 | 0.2 | 0.99 |
| Filling_epsr80_sigma1 | 0.98 | 0.66 | 0.88 |
| Filling_epsr80_sigma2 | 0.98 | 0.47 | 0.89 |
| Filling_epsr80_sigma5 | 1 | 0.3 | 0.9 |
| Filling_epsr80_sigma10 | 1.01 | 0.24 | 0.91 |
| Filling_epsr80_sigma100 | 1.05 | 0.19 | 0.95 |

According to this information, the energy that is introduced into the body of the patient 2 in the region of the shielding apparatus 1, relative to the energy that is introduced above or beneath the shielding apparatus 1, can be significantly reduced, wherein in particular a reduction BY approximately a factor of 5 is possible. The temperature of the electrode lead 4 can be reduced approximately by this factor.

Figure 7:
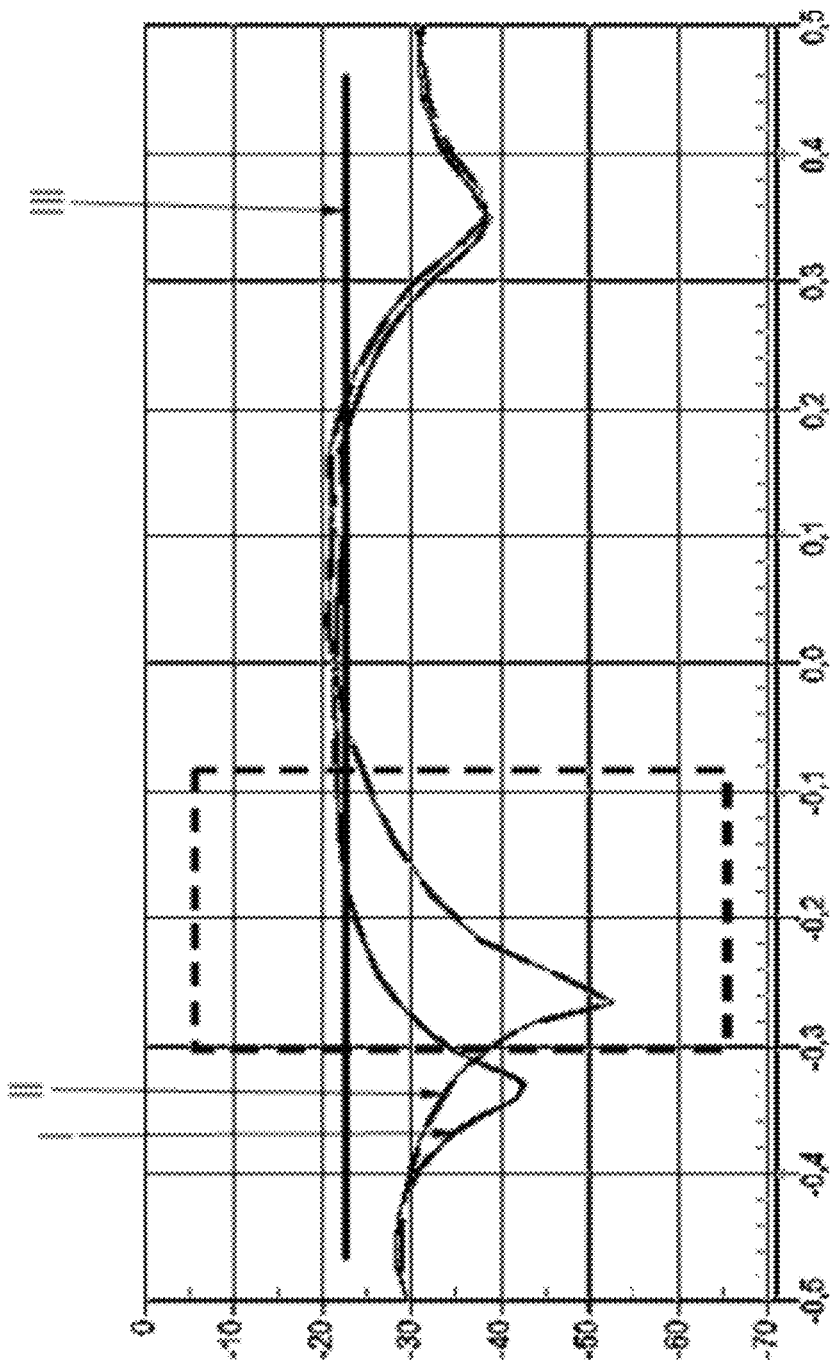
FIG. 7 shows the exemplary curve of the B1 field during an MRI examination with and without the shielding apparatus.

FIG. 7 illustrates the imaging possibilities when using the shielding apparatus according to the invention during an MRI examination. The abscissa indicates the location in m, the ordinate indicates the field strength level dB of the B1 field. The curve I illustrates a situation without the shielding apparatus, while curve II illustrates that with the shielding apparatus. Above curve III, the field strength of the B1 field is sufficient for imaging. The dotted line indicates the region that is shielded. According to this information, the B1 field remains circularly polarized even when shielded, which is to say the x and y components are equally strong and only local attenuation occurs. Only the field of view (FOV=Field Of View) is slightly limited. From this information, it can be concluded that with the shielding apparatus, imaging is still possible up to at least 4 cm in front of the end (edge region) of the shielding apparatus.

As has been explained in detailed based on the exemplary embodiment, the shielding apparatus according to the invention enables a simple, cost-effective MRI examination that is free of risks for the patient, without requiring special precautions on the implant. In particular patients who already have an implant can also undergo an MRI examination, wherein in particular no special adjustments to the magnetic resonance imaging scanner may be required. For example, an ICD can also deliver antitachycardic or antibradycardic treatment in the magnetic resonance imaging scanner. A particular advantageous is the possibility to even shield defective or deactivated probes and long stents, such as vascular prostheses.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE NUMERALS

1 Shielding apparatus
2 Patient
3 Pacemaker
4 Electrode lead
5 Electrode tip
6 Heart
7 Thorax
8 Communication device
9 Signal
10 Shielding material
11 Shielding structure
12 Magnetic resonance imaging scanner
13 Patient cylinder
14 Space
15 Examination table
16 Radio frequency resonator
17 Inside wall

What is claimed is:

1. A shielding apparatus configured to shield at least one at least partially metallic implant in a body of a patient during an examination by magnetic resonance imaging, comprising:
   a shield configured to be externally attached temporarily during an examination by magnetic resonance imaging between an external surface of the body of the patient and a patient cylinder in a magnetic resonance imaging scanner; and,
   wherein said shield comprises a shielding material, which is configured to attenuate radio frequency alternating electromagnetic fields, and further comprises a communication device configured to communicate with the at least one at least partially metallic implant.

2. The shielding apparatus according to claim 1, wherein the shielding material comprises a relative magnetic permeability of no more than 100.

3. The shielding apparatus according to claim 1, wherein the shielding material comprises a relative magnetic permeability of no more than 4.

4. The shielding apparatus according to claim 1, wherein the shielding material comprises a relative magnetic permeability of no more than 1.

5. The shielding apparatus according to claim 1, wherein a physical and/or chemical property of the shielding material is varied so as to vary the attenuation ability thereof.

6. A shielding apparatus according to claim 1, wherein a quantity of the shielding material is varied.

7. A shielding apparatus according to claim 1, wherein said shield is fit on a contour of the external surface of the body the patient.

8. The shielding apparatus according to claim 7, wherein said shield is filled with a gaseous and/or liquid fluid to fit to the contour of the external surface of the body of the patient.

9. A shielding apparatus according to claim 1, wherein said shield comprises a cooling device to cool said shield.

10. The shielding apparatus according to claim 1, wherein said shield comprises a marking device to mark said shield in a magnetic resonance image created during the examination.

11. A shielding structure comprising a shielding apparatus configured to shield at least one at least partially metallic implant in a body of a patient during an examination by magnetic resonance imaging using a magnetic resonance imaging scanner comprising:
   a shield configured to be externally attached temporarily during an examination by magnetic resonance imaging on or outside an external surface the body of the patient; and,
   wherein said shield comprises a shielding material, which is configured to attenuate radio frequency alternating electromagnetic fields, when the patient is located in a patient cylinder of the magnetic resonance imaging scanner and wherein the shield is configured to extend radially toward the patient cylinder, and
   wherein said shield further comprises a communication device configured to communicate with the at least one at least partially metallic implant.

12. The shielding structure according to claim 11, wherein said shield comprises a cylindrical outer contour and wherein the shield is disposed coaxially to a field coil that generates the radio frequency alternating electromagnetic fields.

13. A method for operating a magnetic resonance imaging scanner, which uses radio frequency alternating electromagnetic fields comprising:
   externally attaching a shield temporarily during an examination by magnetic resonance imaging between an external surface of a body of a patient and a patient cylinder in a magnetic resonance imaging scanner; and,
   attenuating radio frequency alternating electromagnetic fields with said shield;
   wherein said shield comprises a shielding material configured to attenuate said radio frequency alternating electromagnetic fields, and further comprises a communication device configured to communicate with the at least one at least partially metallic implant.

14. The method according to claim 13, further comprising cooling the shield at least some of the time during an examination by the magnetic resonance imaging scanner.

15. The method according to claim 13, further comprising attenuating the radio frequency alternating electromagnetic fields during an excitation phase, during which atom nuclei are excited by resonance, and further comprising attenuating the radio frequency alternating electromagnetic fields at least less during a readout phase, during which the atom nuclei relax.

16. A method according to claim 13, further comprising attenuating the radio frequency alternating electromagnetic fields such that said magnetic resonance imaging scanner may be used on the patient having an implant.

17. The shielding apparatus according to claim 1, wherein said communication device is further configured to transmit information to said at least one at least partially metallic implant, and wherein said information comprises one or more of
   information regarding activation of the shield, generation of the radio frequency alternating electromagnetic fields and presence of an MRI examination, and
   information regarding ending of the generation of the radio frequency alternating electromagnetic fields when there is no activity of the communication device.

18. The shielding apparatus according to claim 1, wherein said shield is powered from the radio frequency alternating electromagnetic fields of said magnetic resonance imaging scanner, such that a separate power supply for said communication device is not required, and wherein said communication device only operates during an examination with said magnetic resonance imaging scanner.

19. The shielding apparatus according to claim 10, wherein said mark of said shield enables automatic image correction or artifact delineation.

20. The shielding apparatus according to claim 10, wherein said marking device comprises a radio frequency identification transponder configured to automatically identify and mark said shield using electromagnetic waves.

* * * * *